US005562679A

United States Patent [19]

Valtchev

[11] Patent Number: 5,562,679
[45] Date of Patent: Oct. 8, 1996

[54] COLLAR SYSTEM FOR UTERINE MOBILIZER

[76] Inventor: Konstantin L. Valtchev, 43 Cosmic Drive, Don Mills, Toronto, Ontario, Canada, M3B 3G1

[21] Appl. No.: 268,107

[22] Filed: Jul. 6, 1994

Related U.S. Application Data

[63] Continuation-in-part of Ser. No. 31,375, Mar. 9, 1993, abandoned.

[51] Int. Cl.$^6$ .......................... A61B 17/42; A61B 17/02
[52] U.S. Cl. .......................................... 606/119; 600/201
[58] Field of Search .............................. 606/1, 119–123, 606/190–198, 108; 128/20, 17, 3; 604/55, 164–170, 264, 282; 600/220–223

[56] References Cited

U.S. PATENT DOCUMENTS

| | | |
|---|---|---|
| 1,559,737 | 11/1925 | Bock . |
| 2,482,622 | 9/1949 | Kahn . |
| 3,796,211 | 3/1974 | Kohl . |
| 3,877,433 | 4/1975 | Librach . |
| 3,889,657 | 1/1975 | Baumgartner . |
| 3,948,270 | 4/1976 | Hasson . |
| 4,000,743 | 1/1977 | Weaver . |
| 4,022,208 | 5/1977 | Valtchev . |
| 4,461,280 | 7/1984 | Baumgartner . |
| 4,569,346 | 2/1986 | Poirier . |
| 4,585,438 | 4/1986 | Makler . |
| 4,775,362 | 10/1988 | Kronner . |
| 4,997,419 | 3/1991 | Lakatos . |
| 5,100,382 | 3/1992 | Valtchev . |
| 5,237,985 | 8/1993 | Hodgson et al. .................. 606/119 |

FOREIGN PATENT DOCUMENTS

| | | |
|---|---|---|
| 0169704 | 1/1986 | European Pat. Off. . |
| 0400458 | 3/1991 | European Pat. Off. . |
| 1084427 | 6/1960 | Germany . |

OTHER PUBLICATIONS

Publication—*Valtchev Uterine Mobilzer*, undated, Conkin Surgical Instruments Ltd.

*Primary Examiner*—Gary Jackson
*Assistant Examiner*—Glenn Dawson
*Attorney, Agent, or Firm*—Henderson & Sturm

[57] ABSTRACT

A gynecologic instrument or uterine mobilizer having a tube with one end attached to a journal pivotally mounted and maintained within a channel in the head of the instrument via a pin engaging a groove in the head. The head includes structure, such as an attachment or collar, for manipulating a desired place of a vaginal wall when the instrument is inserted in the vagina. In one embodiment, the structure includes a collar having a concave surface lying over a surface of the head that is substantially crescent-shaped. In another embodiment, the structure includes a substantially disc-shaped element. In one of two related embodiments, the substantially disc-shaped element may be provided with an indentation or notch in a peripheral surface. In another embodiment, the substantially disc-shaped element is provided with a channel extending at least radially from a central portion of the substantially disc-shaped element, and preferably along a diameter of the disc, for housing elements designed to cooperate to move the vaginal wall towards the abdominal cavity.

23 Claims, 12 Drawing Sheets

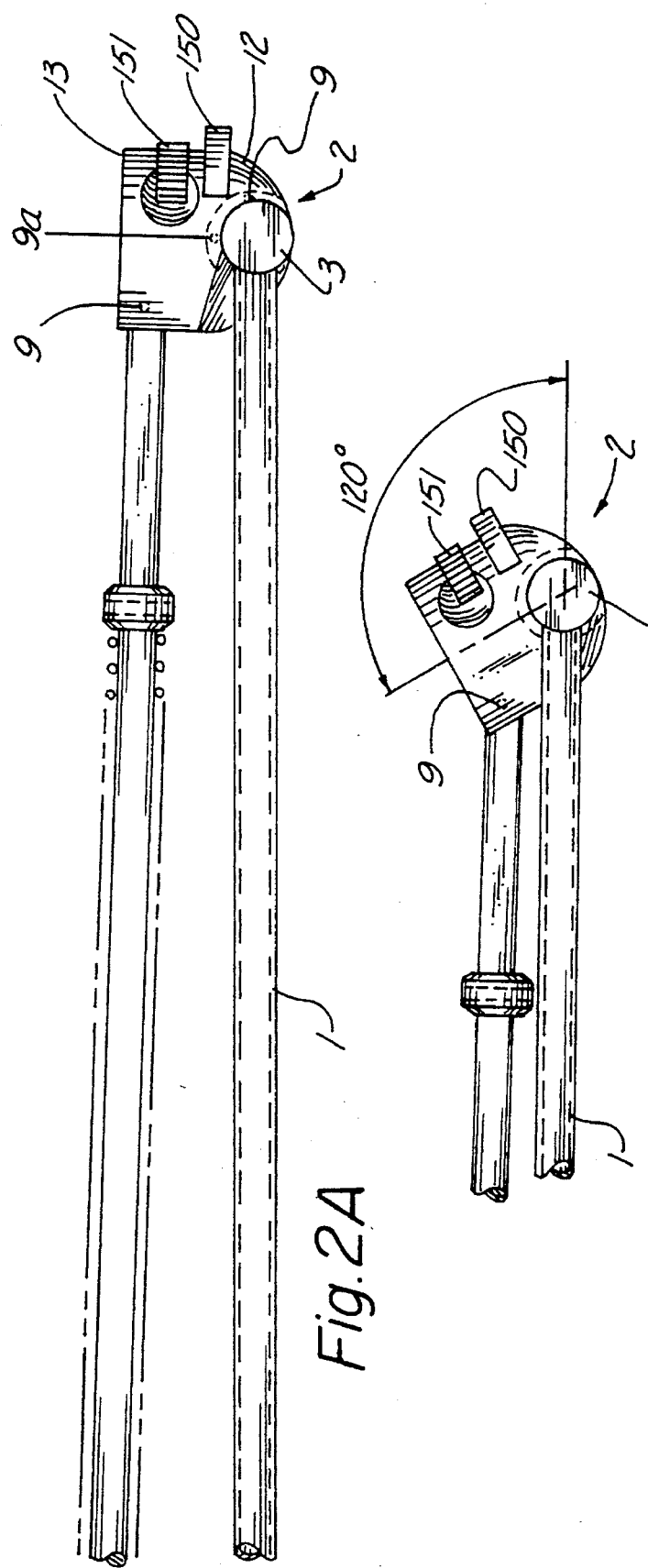

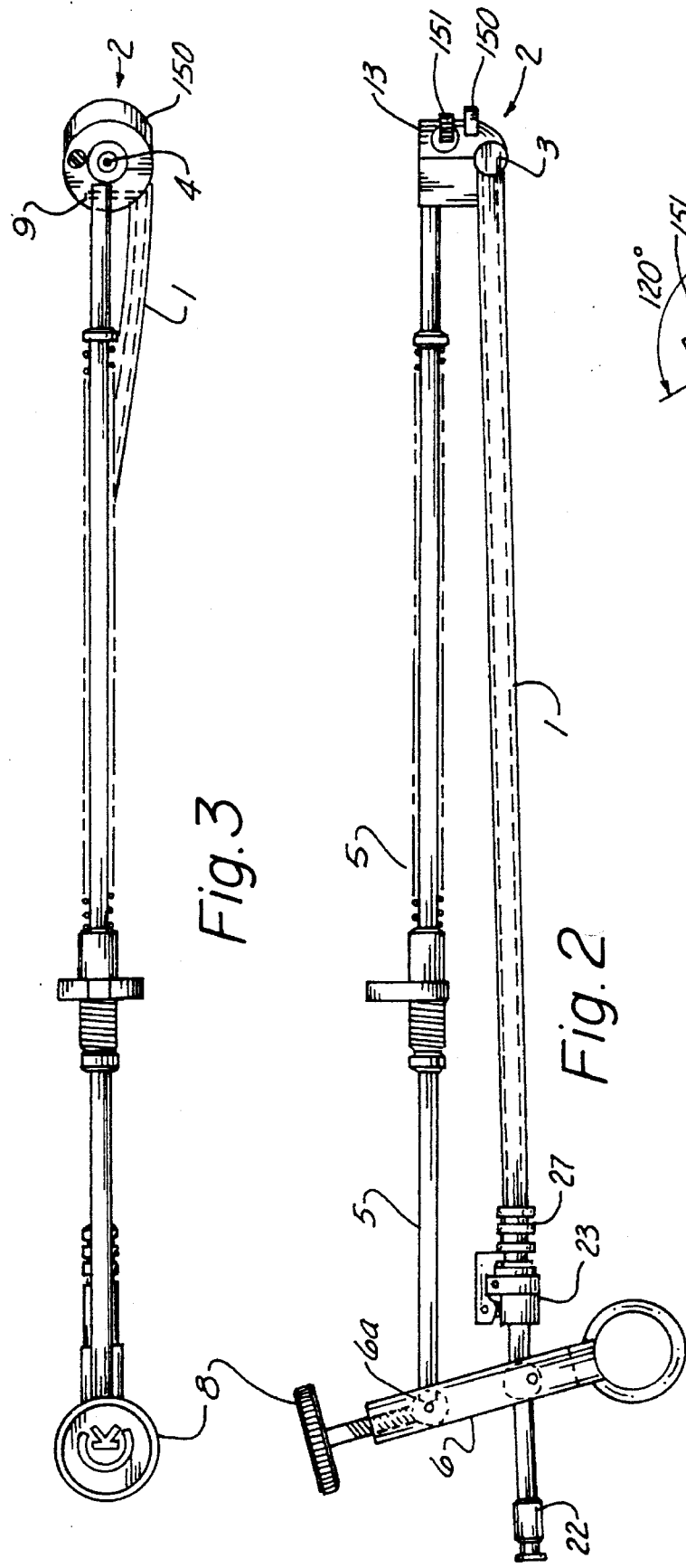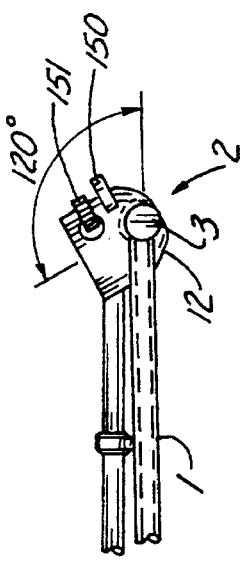

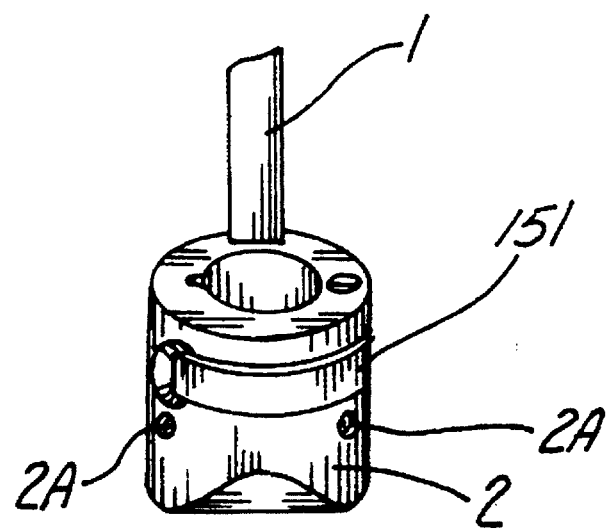
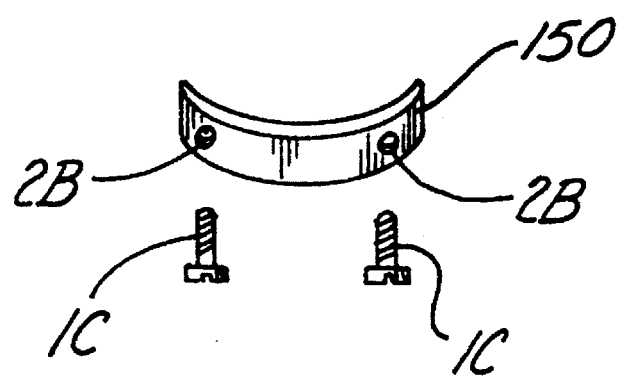
Fig 14A
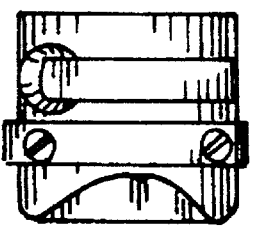
Fig. 14B

COLLAR SYSTEM FOR UTERINE MOBILIZER

RELATED APPLICATION

This application is a Continuation-In-Part of my prior related application U.S. Ser. No. 08/031,375 filed Mar. 9, 1993 for "CONNECTION MECHANISMS FOR UTERINE MOBILIZER", now abandoned, the disclosure of which in its entirety is incorporated herein by reference.

TECHNICAL FIELD

The present invention relates to a gynecologic instrument useful in gynecologic laparoscopy. More particularly, the present invention is directed to a uterine mobilizer or manipulator. Specifically the present invention is directed to an improved uterine mobilizer provided with improved collar for pushing the vaginal wall toward the abdominal cavity.

BACKGROUND ART

In my U.S. Pat. No. 4,022,208, the disclosure of which in its entirety is incorporated by reference herein, I disclose and claim a gynecologic instrument capable of rotating the uterus to any of its natural positions within the peritoneal cavity which instrument lessens the danger of damage to vaginal and uterine tissue and which instrument may be adopted for injection of dye into a uterus while the uterus is maintained in any of its natural positions.

SUMMARY OF THE INVENTION

The present invention is directed to improvements to be embodied in gynelogic instruments that are particularly useful when embodied in the gynecologic instrument disclosed and claimed in U.S. Pat. No. 4,022,208, and my prior related application U.S. Ser. No. 08/031,375, filed Mar. 9, 1993 and entitled "Connection Mechanism For Uterine Mobilizer".

In the apparatus of the present invention, the improvements reside in means for pushing the vaginal wall towards the abdominal cavity.

Accordingly, the present invention is directed to a gynecologic instrument or uterine manipulator having a head wherein the head includes an attachment or collar having a new and unobvious structure for manipulating a desired place of a vaginal wall when the instrument is inserted in the vagina, and wherein the head is attached to one end of a tube by a journal pivotally mounted and maintained within a channel in the head of the instrument via a pin engaging a groove in the head.

In one embodiment, the structure for manipulating a desired place of vaginal wall in accordance with the present invention includes a collar having a concave surface lying over a surface of the head that is substantially semi-lunar in shape.

In another embodiment, the structure for manipulating a desired place of a vaginal wall in accordance with the present invention includes a substantially disc-shaped element.

In one of two related embodiments, the substantially disc-shaped element may be provided with an indentation or notch in a peripheral surface.

In another embodiment, the substantially disc-shaped element is provided with a channel or conduit for housing elements designed to cooperate to move the vaginal wall towards the abdominal cavity.

BRIEF DESCRIPTION OF THE DRAWINGS

The invention will be clearly understood after reference to the following detailed specification read in conjunction with the drawings.

In the drawings:

FIG. 2 is a side view of an apparatus in accordance with the present invention, and FIG. 2a is a partial side view of the head end of the apparatus in accordance with the present invention.

FIG. 3 is a top view of an apparatus in accordance with the present invention.

FIG. 4 is a partial side view of an apparatus in accordance with the present invention showing the head in the fully extended position.

FIGS. 5 and 5a are partial side views of an apparatus in accordance with the present invention showing the head in the fully flexed position.

FIG. 14A is and exploded view showing the relationship between head 2 and the collar 150 of the present invention.

FIG. 14B shows the collar mounted to the head.

DISCLOSURE OF THE INVENTION

Figure 1:
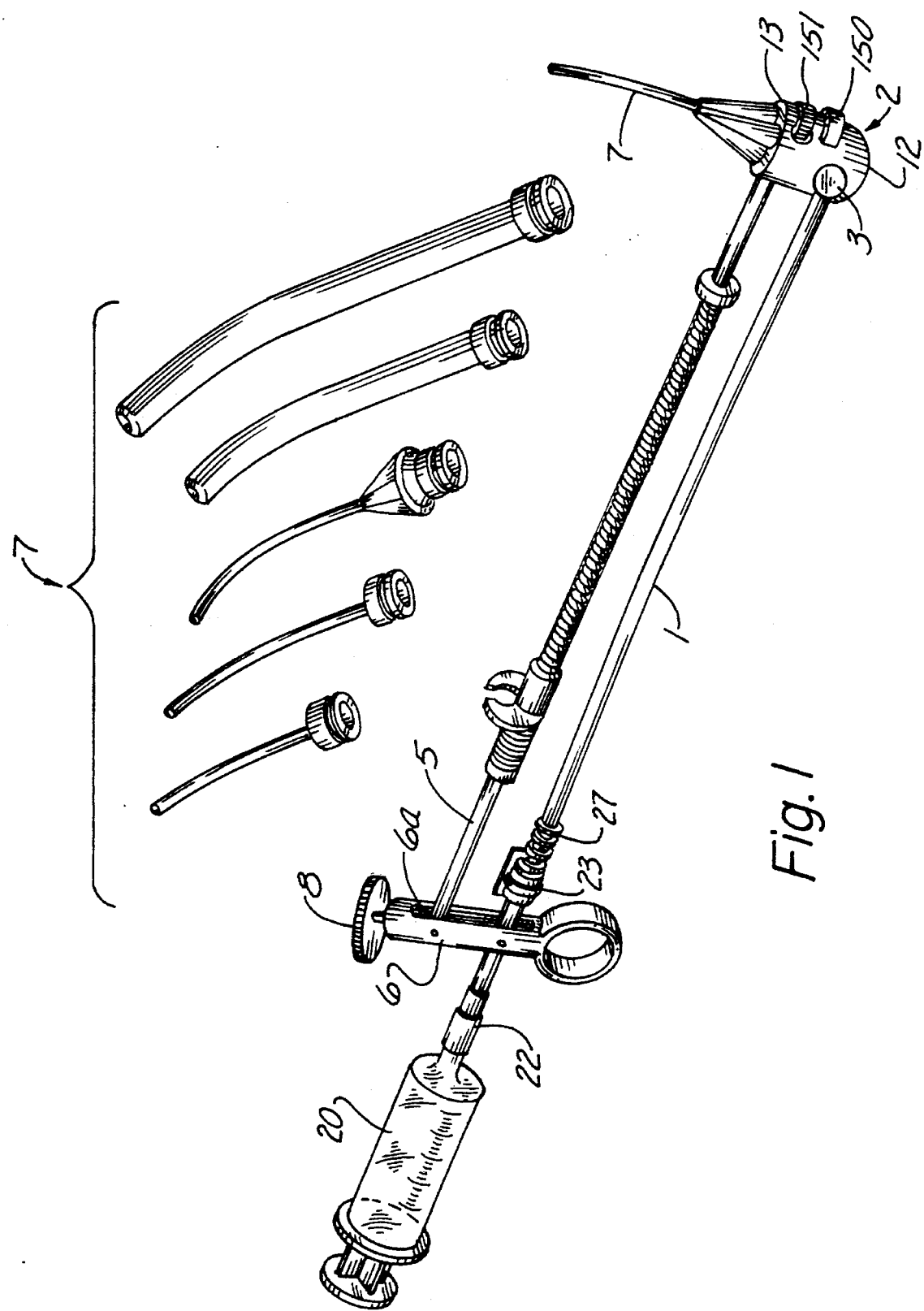
FIG. 1 is a side view elevational of an apparatus in accordance with the present invention.
Figure 6:
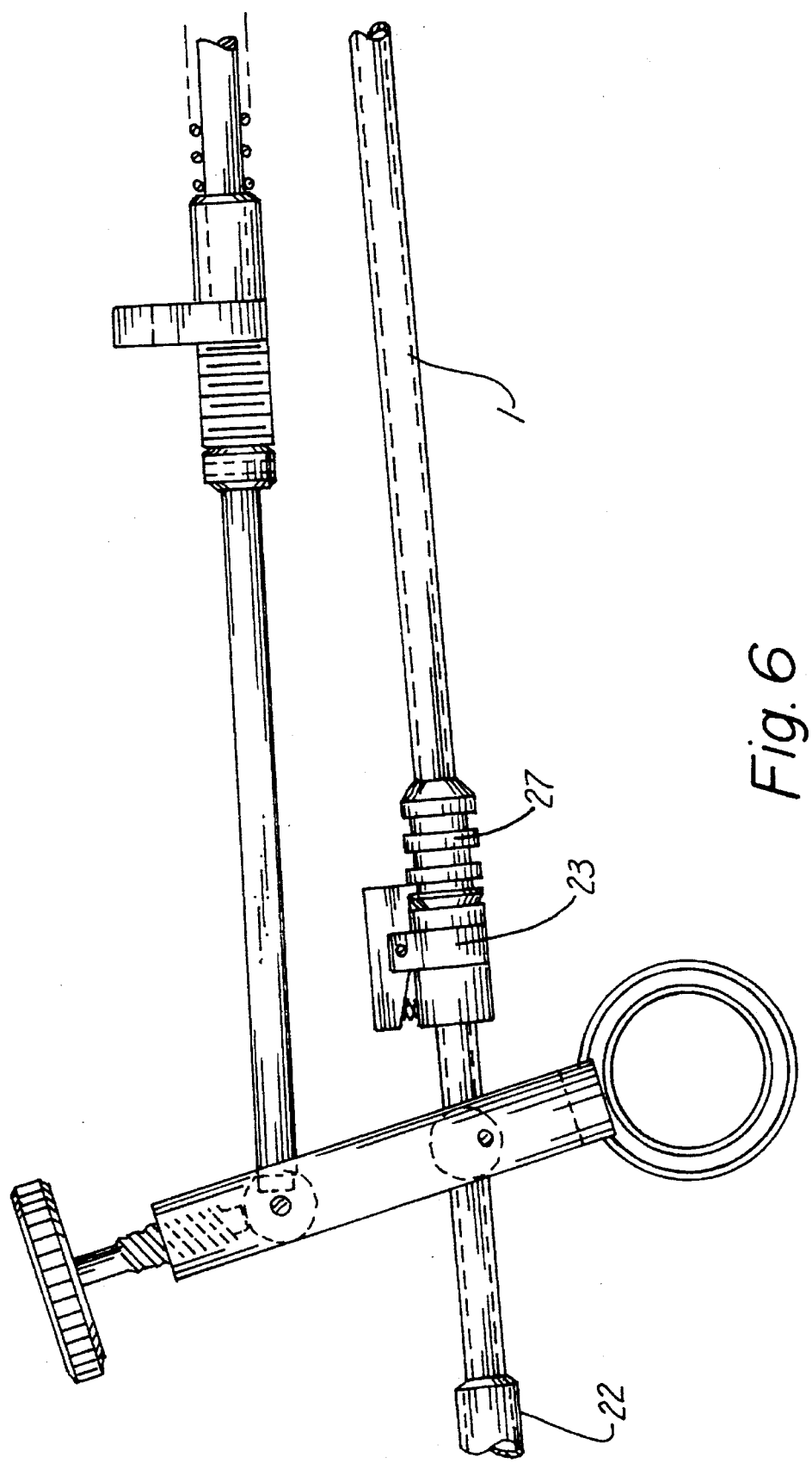
FIG. 6 is a partial side view of the tail end of the apparatus in accordance with the present invention.
Figure 9:
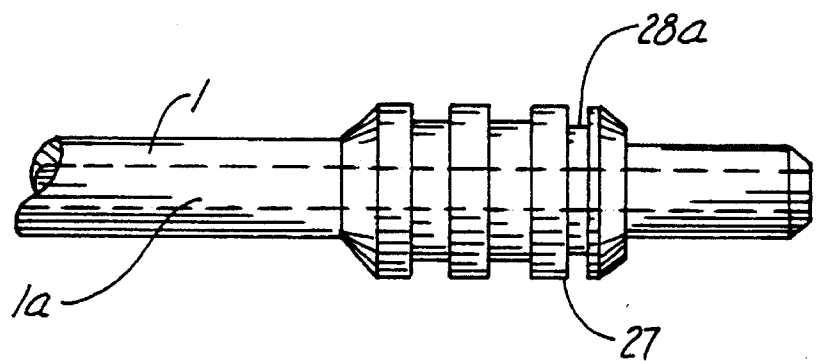
FIG. 9 is a cross-sectional view of the sleeve on the tube for connection with the tube holder of the apparatus of the present invention.
Figure 7:
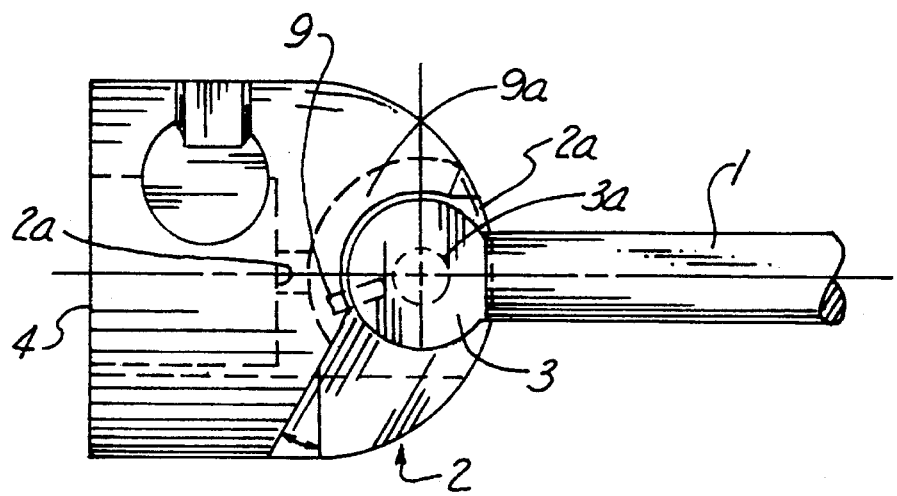
FIG. 7 is a cross-sectional view of the head of the apparatus of the present invention.
Figure 8:
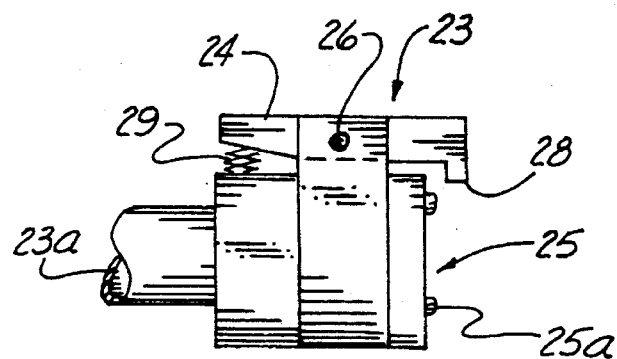
FIG. 8 is a cross-sectional view of the tube holder of the apparatus of the present invention.

The present invention intended to be claimed is described herein below.

The present invention is directed to a gynecologic instrument comprising a tube having a proximal end and a distal end; and a head pivotally connected in a releasable manner by a journal to the proximal end of the tube, the head comprising structure for manipulating a desired place in a vagina, wherein the means for manipulating comprises means for moving a wall of the vagina toward the peritoneal cavity, and wherein the means for moving comprises means for causing a bulge in the vaginal wall.

For purposes of the present invention, as otherwise described herein, the means for manipulating comprises an attachment to the head, which may be semi-lunar in shape. Preferably the attachment may be a collar, and the collar is made of a suitable material, preferably selected from the group consisting of stainless steel and plastic.

For purposes of the present invention, as otherwise described herein, the head comprises a lock, and the collar is attached to the head below the lock. Preferably, the collar is attached to the head, and the head comprises at least one orifice and the collar comprises at least one orifice, wherein the at least one orifice of the head and the at least one orifice of the collar are in alignment when the collar is attached to the head. Preferably, the collar comprises a concave surface lying over a surface of the head. Preferably, the at least one orifice of the head and the at least one orifice of the collar comprise a plurality of orifices, more preferably wherein the plurality of orifices of the head comprise two orifices and the plurality of the orifices of the collar comprise two orifices, most preferably wherein the plurality of orifices are threaded, in which case the gynecological instrument also includes a screw respectively threaded through each of the threaded orifices of the collar and threadedly engaged in each of the threaded orifices of the head.

In accordance with the present invention, as otherwise described herein, in one embodiment, the attachment to the head comprises a substantially disc-shaped element, wherein the substantially disc-shaped element comprises an indentation in a peripheral surface. Preferably, the gynecological instrument also includes an obturator attached to the substantially disc-shaped element, preferably wherein the substantially disc-shaped element comprises at least one conduit extending substantially radially from a central portion of the substantially disc-shaped element to define at least one opening in a peripheral surface of the substantially disc-shaped element.

For purposes of the present invention, as otherwise described herein, the gynecological instrument also includes a stopper fitted in the at least one opening of the conduit, wherein the stopper comprises a threaded circumferential surface, and the conduit comprises an inner surface comprising complementary threads mating with the threaded circumferential surface of the stopper, and preferably also includes at least one piston assembly housed in the channel, wherein the at least one piston assembly comprises a piston head, and an element extending from the piston head through the stopper and fitted to a structure covering the opening of the conduit.

For purposes of the present invention, as otherwise described herein, the gynecological instrument also includes structure for biasing that covers the opening of the conduit to maintain contact with the disc, wherein the structure for biasing comprises a spring, preferably wherein the at least one conduit extends along a diameter of the substantially disc-shaped element, and defines two diametrically opposed openings in a peripheral surface of the substantially disc-shaped element, wherein the at least one piston assembly comprises two piston assemblies, and the piston head of each the two piston assemblies are separated from each other by a space.

In one embodiment of the present invention, as otherwise described herein, the proximal end of the tube is attached to an end of a journal pivotally fitted in an opening in the head along a pivotal axis of the head with respect to the tube. Preferably the head comprises a groove, and the journal comprises a pin for engaging the groove to connect the head to the tube, wherein the groove and the pin are adapted to be disengaged by rotating the tube about the journal by a prescribed degree of rotation.

In a preferred embodiment of the present invention the head comprises a substantially crescent-shaped or semi-lunar shaped collar attached to the head for manipulating a desired place in a vagina, wherein the crescent-shaped or semi-lunar shaped collar comprises a concave surface lying over a surface of the head, and wherein the at least one orifice of the head and the at least one orifice of the crescent-shaped or semi-lunar shaped collar comprise a plurality of orifices, preferably wherein the plurality of orifices are threaded, in which case a screw is respectively threaded through each of the threaded orifices of the crescent-shaped or semi-lunar shaped collar and threadedly engaged in each of the threaded orifices of the head.

For purposes of the present invention, as otherwise described herein, the head comprises a lock, and the crescent-shaped or semi-lunar shaped collar is attached to the head below the lock, preferably wherein the head comprises at least one orifice and the collar comprises at least one orifice, the at least one orifice of the head and the at least one orifice of the crescent-shaped or semi-lunar shaped being in alignment when the collar is attached to the head.

In another preferred embodiment of the present invention the head comprises a substantially disc-shaped element attached to the head for manipulating a desired place in a vagina, the substantially disc-shaped element preferably comprises an indentation in a peripheral surface.

For purpose is of the present invention, as otherwise described herein, the gynecological instrument may also include an obturator attached to the substantially disc-shaped element.

In the embodiment of the present invention wherein the head comprises a substantially disc-shaped element comprising at least one conduit extending substantially radially from a central portion of the substantially disc-shaped element for manipulating a desired place in a vagina, the at least one conduit extending substantially radially from a central portion of the substantially disc-shaped element comprises an end defining an opening in a peripheral surface of the substantially disc-shaped element.

For purposes of the present invention, as otherwise described herein, the gynecological instrument also includes a stopper fitted in the opening of the conduit, wherein the stopper comprises a threaded circumferential surface, and the conduit comprises an inner surface comprising complementary threads mating with the threaded circumferential surface of the stopper.

For purposes of the present invention, as otherwise described herein, the gynecological instrument also includes at least one piston assembly housed in the channel, wherein the at least one piston assembly comprises a piston head, and an element extending from the piston head through the stopper and fitted to a structure covering the opening of the conduit.

For purposes of the present invention, as otherwise described herein the gynecological instrument also includes structure for biasing the structure covering the opening of the conduit to maintain contact with the disc, wherein the structure for biasing comprises a spring, and preferably wherein the at least one conduit extends along a diameter of the substantially disc-shaped element, and defines two diametrically opposed openings in a peripheral surface of the substantially disc-shaped element, wherein the at least one piston assembly comprises two piston assemblies, and the piston head of the two piston assemblies are separated from each other by a space.

The present invention will now be described in more detail in reference to the attached drawings which illustrate by non-limiting example a preferred embodiment of the present invention.

The instrument illustrated in the Figures has a stem, tubing, or tube 1 and a block or head 2 pivotally mounted on the tube by piston 3.

The head 2 of the apparatus of the present invention is provided with a channel 2a for receiving a journal 3 adapted to rotate or pivot about its axis in the channel 2a. The head is also provided with a groove 9a for receiving a pin 9 attached to the journal 3 for engaging the groove 9a to connect the head 2 to the tube. The pin 9 attached to the journal 3 when inserted in the groove 9a in the head 2 are adapted to prevent removal of the journal 3 from the channel 2a in the head 2 when the pin 9 is positioned within the groove. The pin 9 and the groove 9a are disengaged by rotating the tube 1 attached to the journal 3 by a prescribed degree of rotation, preferably about 155°, until the pin becomes free of the groove to permit the journal 3 to which the tube 1 is attached to be pulled out of the head 2.

Accordingly, the apparatus of the present invention differs from generally similar apparatus in the way in which the tube is attached to the head. In accordance with the apparatus of the present invention, the tube is first disengaged from the tube holder, rotated to about 155°, and pulled out from the head. However, the pin which is attached to the tube and is engaged in the grove of the head remains engaged during the range of movement at the time of surgery.

As shown in the Figures, tube holder 23 is provided at one end with a luer syringe connector 22 which in turn is connected to a syringe 20. At the opposite end of the tube connector 23 there is a cylindrical cavity 25 having an entrance in which an "O" ring 25a is positioned for receiving the distal end of tube 1. The tube holder 23 is provided with a locking mechanism 24 pivotally attached to the tube holder by a pin or other means 26 which permits rotation of the locking mechanism thereabout. The locking mechanism 24, at the end which points towards the sleeve 27, has a tooth 28 which engages the first groove 28a of the sleeve and locks it in place. The locking mechanism is adapted to pivot about axis 26 in a seesaw or reciprocal manner. To this end, a spring or other means for biasing 29 is provided at one end of the locking mechanism 24 which pushes the locking mechanism up and consequently pushes the tooth downward into the groove at the opposite end of the tube holder.

Figure 10:
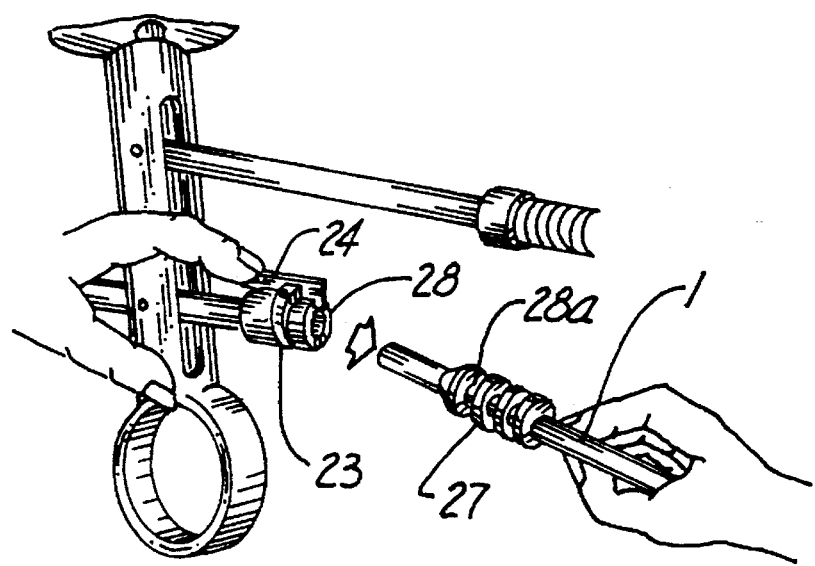
FIG. 10 is an illustration of removing the tube from the tube holder of the apparatus in accordance with the present invention.

As illustrated in FIG. 10, to remove the tube 1 from the tube holder 23, one merely needs to push the end of the locking mechanism 24 over the spring downwardly compressing the spring and lifting the tooth 28 of the locking mechanism up from the groove 28a of the sleeve 27. This releases the sleeve 27 and the tube 1 can be pulled out from the tube holder 23.

As long as the tube 1 is locked into the tube holder 23 during the manipulation of the head 2 from the straight position to a rotation of 120° as shown in FIGS. 2, 4, 5, and 5A, the pin 9 is engaged in the groove 9a of the head 2 and the journal or piston 3 can not be removed.

The tube 1 can be completely separated from the tube holder 23 and the head 2 in the following way.

Figure 11:
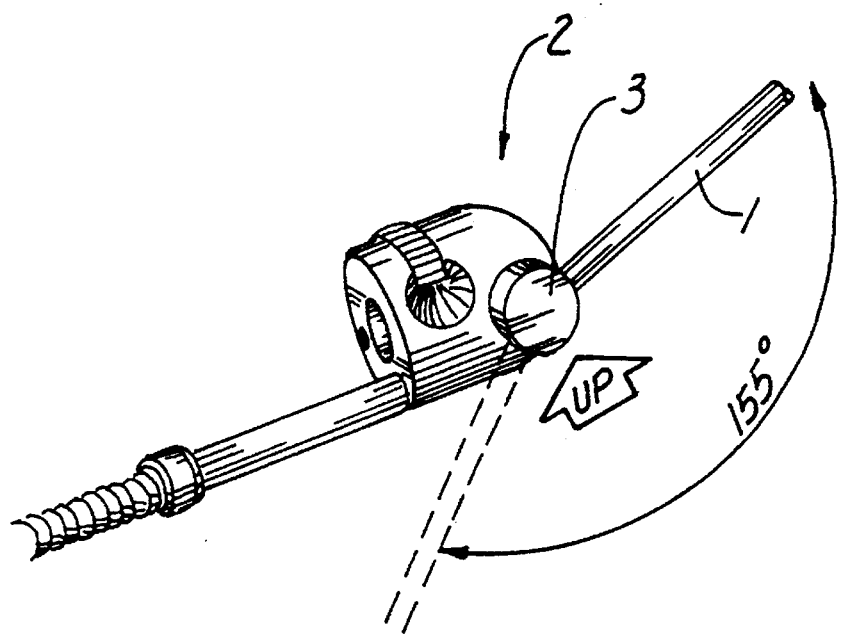
FIG. 11 is an illustration of removing the tube from the head of the apparatus in accordance with the present invention.

The tube 1 is removed from the tube holder 23 as described above; then the tube 1 is rotated counterclockwise as shown in FIG. 11. At that point the pin 9 becomes disengaged from groove 9a, journal piston 3 is in a position to be pulled out from the head 2. To re-attach the tube simply follow the removal procedure in reverse order.

In operation all of the elements of the instrument from syringe 20 to hook 7 include passageways, channels or conduits (whether or not clearly shown) to permit the passage of fluid from the syringe, out of the end of hook 7. Thus, fluid may be injected from the syringe 18 into the channel of the extension tube 23a of tube holder 23 and in turn through the channel 1a in tube 1, piston 3a, head 2a, and from there into the cannula 7 which is inserted in cavity 4 and locked into the head.

Head 2 has a substantial flat cervix engaging shoulder that is adapted to abut the vaginal part of the uterine cervix. A recess or cavity 4 is provided in head 2 to receive an obturator, cannula or equivalent device designated generally as hook 7 in U.S. Pat. No. 4,022,208 and shown in FIG. 1 as such. The control link 5 has an extension or spacer bar 6 at its free end. The spacer bar 6 has a through bore 6a so that it can move relative to tube 1. A thumb screw or lock screw 8 threadedly engages in spacer bar 6 and can be turned to tighten against tube 1 to lock the link 5 with respect to tube 1 and fix the angular position of head 2 and hook 7 with respect to tube 1. Thus, the hook 7 can be manipulated to any desired angular position with respect to the tube 1 and maintained in that position by the set thumbscrew 8.

Head 2 includes a substantially partially spherical surface 12 opposite shoulder 13. This surface must be smooth in order to minimize the chances of injury to sensitive vaginal tissue during rotation of head 2 about journal or piston 3. A partial spherical surface is the most desirable shape although other smooth contours may be employed. As the uterus is moved by the movement of cannula 7, ligaments attached to the uterus may cause the instrument to be pressed against the vaginal wall. Thus, the smooth partially spherical surface will distribute any such pressure and support the instrument and uterus throughout the full range of possible positions. Shoulder 13 ensures that excess penetration of cannula 7 will not occur during movement of the uterus. A range of sizes of cannula obturator or similar devices 7, as shown in FIG. 1, may be provided to accommodate any particular patient or condition. A properly chosen size of the cannula or equivalent device and the action of shoulder 13 will together eliminate the danger of perforating the uterus during use of the instrument.

In a preferred embodiment of the present invention, the head 2 is provided with an attachment 150, shown generally in FIGS. 2, 4, and 5, and in more detail in FIGS. 2A and 5A. Although attachment 150 is illustrated to have a crescent-shape or shape of a half-moon as a semi-lunar attachment, other shapes may be employed that would function in a similar manner. The attachment 150, also referred to herein as collar 150, is preferably made of surgical steel. i.e., stainless steel, however, any material that is acceptable for surgical or other medical procedures, such as plastic, may be employed.

The attachment 150 functions in opening the vagina at the desired place during laparoscopic-assisted, vaginal hysterectomy. As shown, in FIGS. 2, 2A, 4, 5 and 5A, crescent-shaped piece or the semi-lunar piece, of stainless steel is attached to head 2 of the mobilizer below lock 151. The relationship of the crescent-shaped or semi-lunar attachment 150 and lock 151 in head 2, is shown in more detail in FIGS. 14A and 14B.

As shown in FIG. 14A, the collar 150 is provided with two holes or orifices 2B that are positioned to align with two holes or orifices 2a in head 2. The orifices 2a in the head and orifices 2b in the collar are threaded. The concave surface of the collar 150 lies over the head in such a way that threaded orifices 2b align with the threaded orifices 2a. The collar 150 is maintained in position on head 2 by threaded screws 1c which pass through orifices 26 and 2a thus attaching collar 150 to head 2. FIG. 14B shows the collar 150 mounted on head 2.

In operation, when the instrument is fully flexed, as shown in FIG. 5 and FIG. 5A, the crescent-shaped or semi-lunar collar 150 pushes the vaginal wall toward the abdominal cavity. The collar 150 thus functions in permitting the vagina to be opened at a desired place. The advantages of the collar 150 include improving the visibility of the surgeon during laparoscopic assisted vaginal hysterectomy. For example, when the vaginal wall is pushed towards the abdominal cavity, the physician looking through the laparoscope can see the area of the vaginal wall very well distinguished form the surrounding area because of its appearance.

Figure 15:
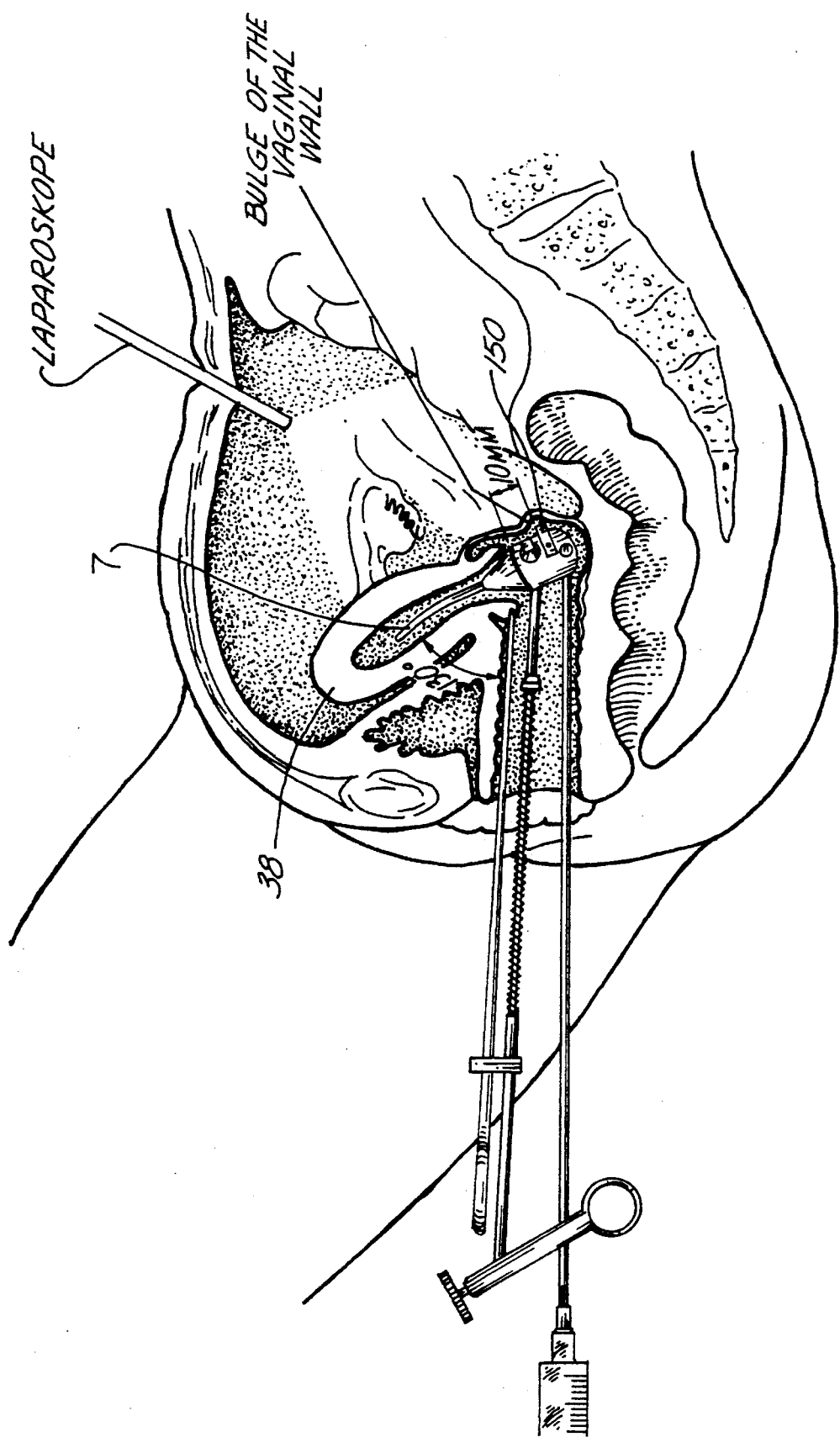
FIG. 15 is a schematic view of the apparatus of the present invention during laparoscopy.

This may be better understood by reference to FIG. 15 which illustrates the mechanism of action of the collar 150 during laparoscopy. After the uterus is anteverted to about 130 degrees the collar 150 pushes the vaginal wall toward the peritoneal cavity. This creates a visible indentation or bulge 38 which can be easily identified by the surgeon who is looking through the laparoscope. Because the distance between the collar and the cervix is 10 mm the surgeon can use this as a marker and place the incision of the vagina in the desired place.

A control link 5 pivotally connects the proximal end thereof with the head 2 by pin 9 and extends from its pivotal connection therewith to adjacent the free distal end of the tube 1. Tube 1 may be provided with a grip (not shown) at the distal end thereof. Preferably such a grip can include a syringe 20. The free distal end of tube 1 may also :be provided with a grip, such as the one identified as element 2 in the U.S. Pat. No. 4,022,208. In either case, a surgeon can, by moving the grips or the distal ends of the spacer bar 5 and tube 1 away from or towards each other in the directions of the arrows 22, rotate head about its pivotal connection with the tube. Thus, a cannula or equivalent device 7 can be caused to move from one dotted line position shown in FIGS. 12, and 13, though the solid line position to the other dotted line position whereby to move the cannula to any desired angular position with respect to the tube. While a greater arc of rotation may be provided the instrument will usefully serve its intended function if the head is pivoted so as to permit movement of the cannula through an arc of at least approximately 135°. To achieve full natural rotation of the uterus, link 5 must be capable of pivoting the cannula from a position where the tube and cannula are substantially parallel to a position where the angle between the tube and the cannula is not greater than about 45°. This is described in more detail in U.S. Pat. No. 4,022,208.

Figure 13:
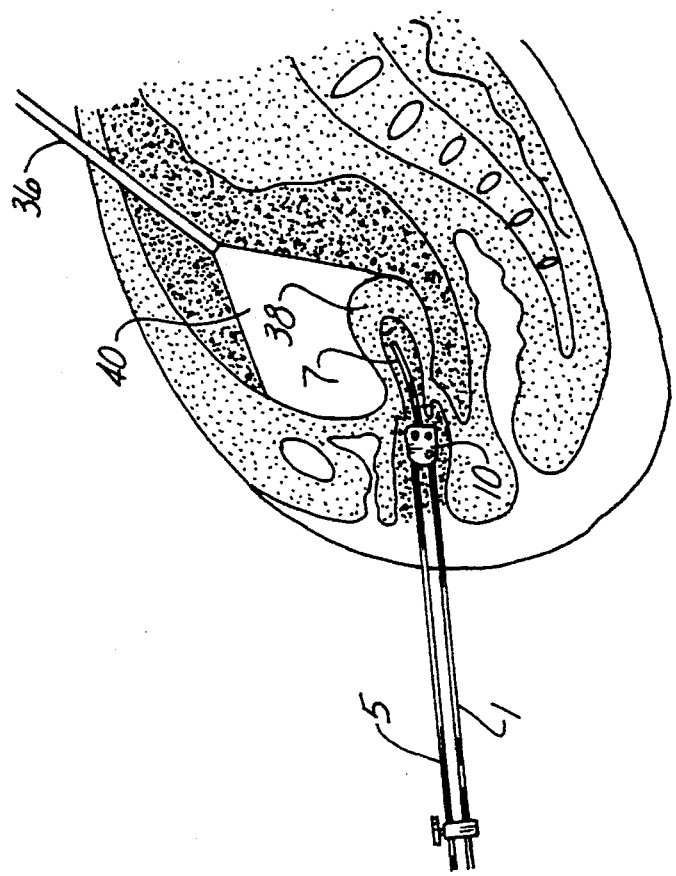
FIGS. 12 and 13 are schematic illustrations of the general manner of use of the apparatus in accordance with the present invention.
Figure 12:
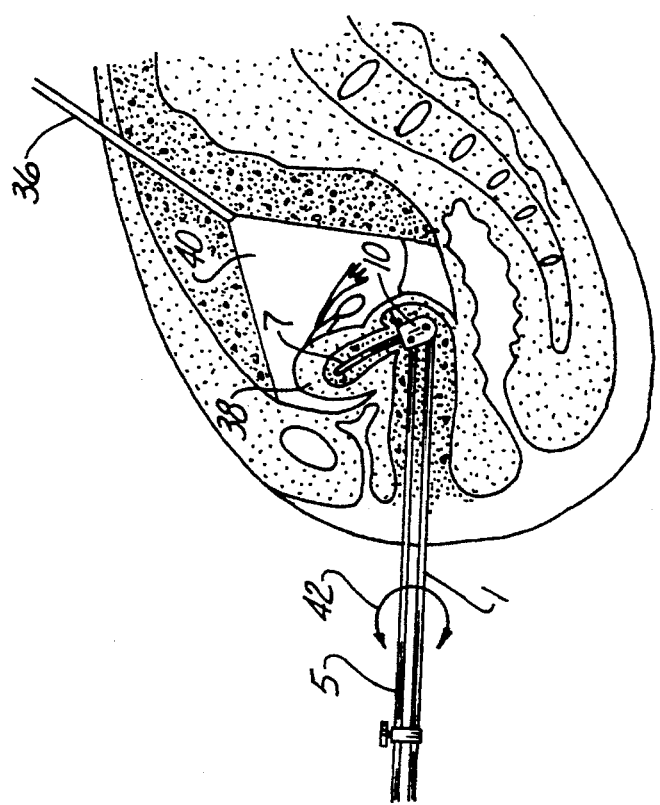

FIGS. 12 and 13 are schematic illustrations of a gynecologic laparoscopy showing the patient in Trendelenburg position, as disclosed in U.S. Pat. No. 4,022,208, and the laparoscope 36 in position to view the uterus 38. The field of vision of the laparoscope is indicated by the numeral 40. The instrument may be used in association with a tenaculum in the conventional manner. Coil spring 15 would on control link 5 and sliding fitting or tenaculum holder 16 for a tenaculum facilitate such use.

The obturator, cannula, or hook 7 of the instrument is inserted into the uterus through the vaginal opening until the cervix engaging shoulder 12 abuts against the cervix of the uterus. Shoulder 12 thus limits the depth of penetration of obturator 7 into the uterus and also supports the uterus as it is moved to the desired position. By manipulation of link 5 and tube 1, e.g. via grips provided at their distal ends; towards or away from each other a surgeon can support the uterus in any position in a vertical or medium sagittal plane from the one illustrated in FIG. 12 to the one illustrated in FIG. 13. This range of vertical positioning gives excellent opportunity for laparoscope inspection. As shown in FIG. 12, the uterus may be flexed to the natural position closest to the abdominal wall. By tightening thumb screw 8 one can fix the obturator 7 in any desired angular position with respect to the tube 1. Thus, the uterus may be maintained at any desired position in the vertical or median sagittal plane. After the uterus has been located in a desired position, the instrument may be rotated about the longitudinal axis of tube 1 in the direction of the arrow 42 shown in FIG. 12. Thus, the uterus may be rotated either to the left or right while close to the abdominal wall giving the surgeon an excellent lateral view.

As disclosed above, the instrument facilitates injection of gases or liquid into the uterus when the obturator 7 is tubular in nature and tube 1 is provided at its distal end with a syringe 20 for providing a gas or liquid through tube 1 which thus functions as a conduit to the head of the obturator 7 as a gas or liquid supply line as disclosed in U.S. Pat. No. 4,022,208.

Related to this, as disclosed in U.S. Pat. No. 4,022,208, a tubular hook 7a may be provided with openings 24 for passage of fluid. The hook 7a may be provided with a tubular extension 15 by means of which a flexible conduit 16 may be fluidly connected to hook 7a. The conduit advantageously passes from the end of such a tubular portion 15 of hook 7a through a fluid passageway in piston 3 through head 2 and thence in a direction parallel to tube 1. Fluid can then be passed through the tube by means of a syringe 18 or other conventional means. Such a modified instrument provides the gynecologist with the ability to inject gases or liquids including dyes while the uterus is maintained in any of its natural positions.

In operation, the collar system for the uterine manipulator of the present invention functions in the following manner. When the instrument is fully flexed the crescent-shaped or semi-lunar collar 150 pushes the vaginal wall toward the abdominal cavity. The collar 150 thus functions in permitting the vagina to be opened at a desired place.

The advantages of the collar 150 include improving the visibility of the surgeon during laparoscopic assisted vaginal hysterectomy. For example, the vaginal wall is pushed towards the abdominal cavity, the physician looking through the laparoscopic can see the area of the vaginal wall very well distinguished from the surrounding area because of its appearance. As previously described, after the uterus is anteverted to about 130 degrees the collar 150, after the uterus is anteverted to about 130 degrees the collar 150, pushes the vaginal wall toward the peritoneal cavity. This creates a visible bulge 38 which can be easily identified by the surgeon who is looking through the laparoscope. Because the distance between the collar and the cervix is 10 mm the surgeon can use this as a marker and place the incision of the vagina in the desired place.

Figure 16:
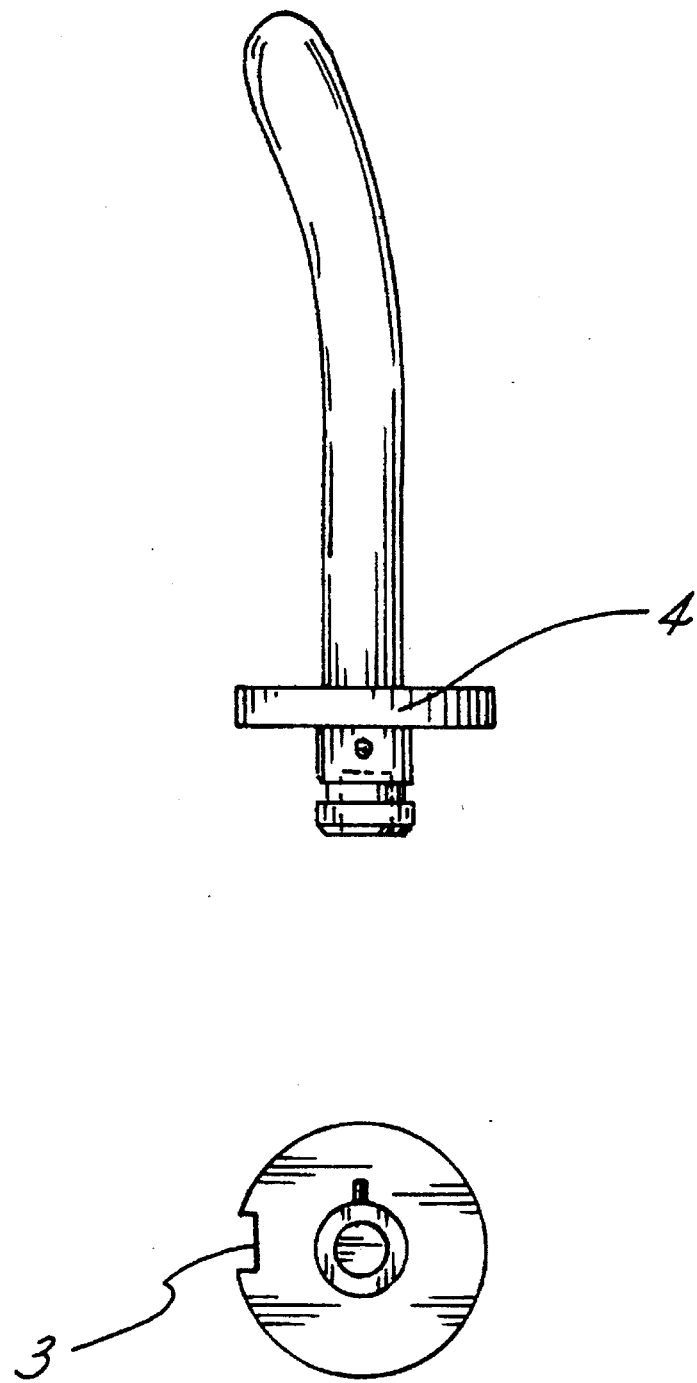
FIG. 16 shows an alternative embodiment of the present invention wherein the collar has a substantially circular or disc shape.

FIG. 16 illustrates another embodiment of the present invention wherein instead of attaching a collar to the head of the instrument, as previously described, the collar instead of being crescent-shaped or semi-lunar is substantially disc-shaped having a substantially circular surface with a diameter larger than the diameter of the head.

This substantially disc-shaped collar has a notch 203, in which the rod 1, is accommodated when the instrument is flexed at the angle of approximately 130 degrees as shown in FIG. 12. This collar 250 can be attached to one of the obturators by drilling an appropriate size hole in the middle, and thereafter soldering it to,the obturator. Alternatively, the collar 250 and the obturator can also be machined as one piece.

An advantage of collar 250, as previously described is that no modifications of the head are necessary. That means that the conventional uterine mobilizers can accommodate the collar 250.

Another advantage is that the cervix lies on the surface of the collar and the bulge which is seen is flush with the surface of the cervix. This eliminates the need for the surgeon to measure the distance between the cervix and the collar when making an incision.

Another advantage is that the bulging in the wall of the vagina will,be visible all around the cervix not only posteriorly which will make the opening of the vagina possible in any place around the cervix.

Figure 17:
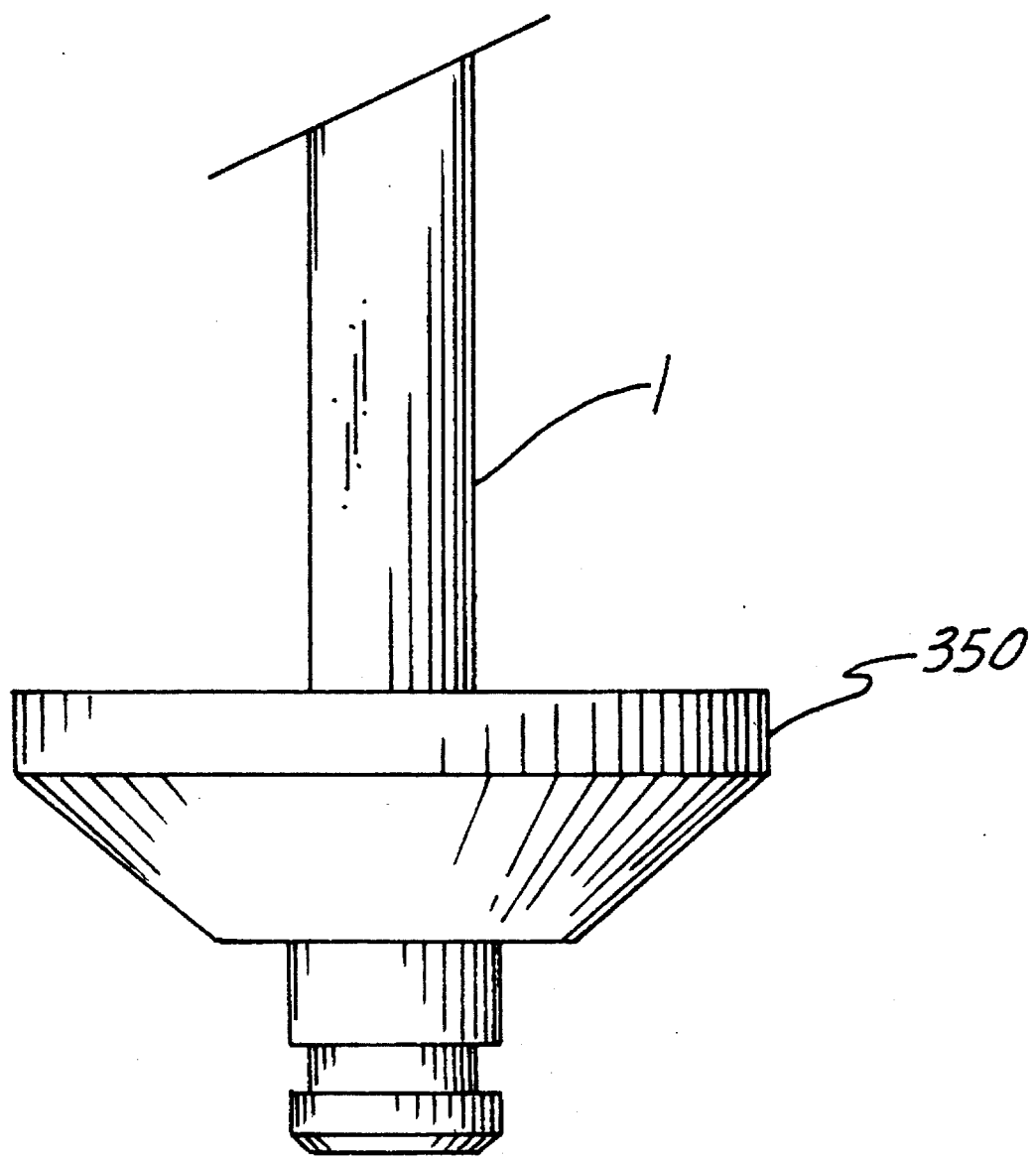
FIG. 17 shows an alternative embodiment of the present invention wherein the disc-shaped element is not provided with an indentation.

In FIG. 17, an alternative embodiment of the present invention is illustrated. In this embodiment, the disc-shaped obturator 350 is not provided with a groove or notch that is provided on the peripheral surface of disc-shaped obturator 250 in the embodiment shown in FIG. 16.

Figure 18:
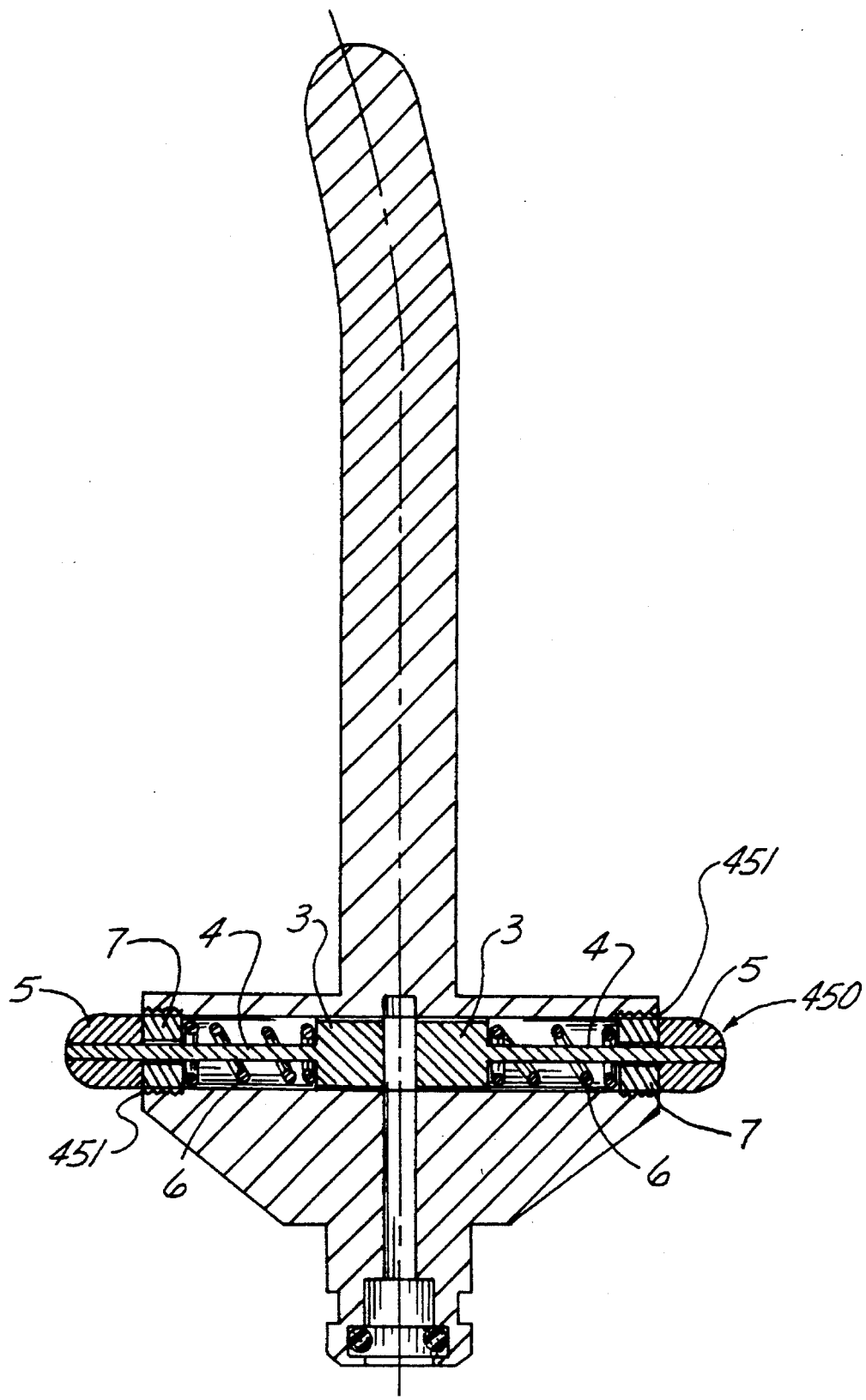
FIG. 18 shows an alternative embodiment of the present invention wherein the substantially disc-shaped element is provided with a channel or conduit for housing elements designed to cooperate to move the vaginal wall towards the abdominal cavity.

FIG. 18 illustrates another embodiment of the collar system of the present invention. In this embodiment, the disc-shaped obturator 450 is provided with a channel 451 extending radially from a central portion of the disc, preferably along a diameter of the disc, from one peripheral surface of the disc-shaped element to the other, and define openings in the peripheral surface of the disc-shaped element.

In this channel 451 are housed two pistons 403 that include piston heads which do not touch each other (there are a few millimeters between them). The piston includes an element that extends from the piston head as a pin 404 which goes through a stopper or washer 407 which has a thread that connects the washer to the disc. The pin at the opposite end of the piston is welded to a structure covering the opening of the conduit, such as a small ball 405. Springs 406 keep the structure covering the opening of the conduit in contact with the disc.

When this obturator is attached to the head and the instrument is inserted into the uterus, one end will face the abdomen of the patient and the other end will face her back anterior and posterior).

This system works in the following way: This obturator is attached to the head of the uterine manipulator and is inserted into the uterus during pelviscopic operations. When the uterus is anteverted the disc creates a bulge of the vagina which the surgeon can see through the laparoscope as has been described herein. Sterile solution is injected into this cannula. The pressure created will push the pistons outward and the balls will protrude and move the vaginal wall further toward the abdominal cavity. If the pressure fluctuates the pulsation of the vaginal wall created by the movement of the ball will be much more visible than the bulge created by the disc. If the uterus is moved backward the same will be visible on the anterior vaginal wall also.

The general method of performing a gynecologic laparoscopy is well known and not referred to in detail. It is well described in the book, "Laparoscopy, Culdoscopy and Gynecography," by Melvin R. Cohen, published 1970 by W. B. Saunders Company of Philadelphia, Pa. London, Ontario and Toronto, Ontario.

It will be appreciated to those of ordinary skill in the art that, while the present invention has been described herein by reference to particular means, methods, and materials, the scope of the present invention is not limited thereby, and extends to any and all other means, methods, and materials suitable for practice of the present invention.

What is claimed is:

1. A gynecologic instrument comprising:
   a) a tube having a proximal end and a distal end; and
   b) a head pivotally connected in a pivotally releasable manner by a journal comprising a pin to the proximal end of the tube, said head comprising a crescent-shaped collar for manipulating a desired place in a vagina, said collar being made of a material selected from the group consisting of stainless steel and plastic, an opening along a pivotal axis of the head with respect to the tube for receiving the journal and a groove for receiving the pin, said journal, being pivotally fitted in the opening and the pin engaging the groove.

2. The gynecologic instrument of claim 1, wherein said crescent-shaped collar comprises means for moving a wall of the vagina toward the peritoneal cavity.

3. The gynecologic instrument of claim 2, wherein said means for moving comprises means for causing a bulge in the vaginal wall.

4. The gynecological instrument of claim 1, wherein said head comprises a lock.

5. The gynecological instrument of claim 4, wherein said collar is attached to said head at a position separate from said lock.

6. The gynecological instrument of claim 1, wherein said collar is attached to said head, and said head comprises at least one orifice and said collar comprises at least one orifice, said at least one orifice of said head and said at least one orifice of said collar being in alignment when said collar is attached to said head.

7. The gynecological instrument of claim 6, wherein said at least one orifice of said head Comprise a plurality of orifices and said at least one orifice of said collar comprise a plurality of orifices.

8. The gynecological instrument of claim 7, wherein said plurality of orifices of said head comprise two orifices and said plurality of said orifices of said collar comprise two orifices.

9. The gynecological instrument of claim 8, wherein said two orifices of said head and said two orifices of said collar are threaded.

10. The gynecological instrument of claim 9, further comprising a screw respectively threaded through each of said threaded orifices of said collar and threadedly engaged in each of said threaded orifices of said head.

11. The gynecological instrument of claim 1, wherein said collar comprises a concave surface lying over a surface of said head.

12. The gynecological instrument of claim 1, further comprising:

c) a tube holder fitted in a releasable manner to the distal end of the tube.

13. The gynecologic instrument of claim 12, wherein said tube holder comprises a means for engaging a fitting on said distal end of said tube.

14. A gynecologic instrument comprising:

a) a tube having a proximal end and a distal end; and b) a head pivotally connected in a pivotally releasable manner by a journal comprising a pin to the proximal end of the tube, said head comprising a substantially disc-shaped collar having an indentation in a peripheral surface; said head further comprising an obturator attached to said substantially disc-shaped collar, wherein said substantially disc-shaped collar further comprises at least one conduit extending substantially radially from a central portion of said substantially disc-shaped collar to define at least one opening in a peripheral surface of said substantially disc-shaped collar; said head further comprising a journal opening along a pivotal axis of the head with respect to the tube for receiving the journal, and a groove for receiving the pin, said journal being pivotally fitted in the journal opening and the pin engaging the groove.

15. The gynecological instrument of claim 14, further comprising a stopper fitted in said at least one opening of said conduit.

16. The gynecological instrument of claim 15, wherein said stopper comprises a threaded circumferential surface, and said conduit comprises an inner surface comprising complementary threads mating with said threaded circumferential surface of said stopper.

17. The gynecological instrument of claim 15, further comprising at least one piston assembly housed in said conduit.

18. The gynecological instrument of claim 17, wherein said at least one piston assembly comprises a piston head, and an element extending from said piston head through said stopper and fitted to a structure covering said opening of said conduit.

19. The gynecological instrument of claim 18, further comprising structure for biasing the structure covering said opening of said conduit to maintain contact with said disc.

20. The gynecological instrument of claim 19, wherein said structure for biasing comprises a spring.

21. The gynecological instrument of claim 20, wherein said at least one conduit extends along a diameter of said substantially disc-shaped element, and defines two diametrically opposed openings in a peripheral surface of said substantially disc-shaped element.

22. The gynecological instrument of claim 21, wherein said at least one piston assembly comprises two piston assemblies.

23. The gynecological instrument of claim 22, wherein said piston head of each said two piston assemblies are separated from each other by a space.

* * * * *